US010055843B2

United States Patent
Tajbakhsh et al.

(10) Patent No.: US 10,055,843 B2
(45) Date of Patent: Aug. 21, 2018

(54) SYSTEM AND METHODS FOR AUTOMATIC POLYP DETECTION USING CONVULUTIONAL NEURAL NETWORKS

(71) Applicants: MAYO FOUNDATION FOR MEDICAL EDUCATION AND RESEARCH, Rochester, MN (US); ARIZONA BOARD OF REGENTS on Behalf of Arizona State University, Scottsdale, AZ (US)

(72) Inventors: Nima Tajbakhsh, Tempe, AZ (US); Suryakanth R. Gurudu, Phoenix, AZ (US); Jianming Liang, Phoenix, AZ (US)

(73) Assignees: Mayo Foundation for Medical Education and Research, Rochester, MN (US); Arizona Board of Regents on behalf of Arizona State University, Scottsdale, AZ (US)

( * ) Notice: Subject to any disclaimer, the term of this patent is extended or adjusted under 35 U.S.C. 154(b) by 0 days.

(21) Appl. No.: 15/562,088

(22) PCT Filed: Mar. 31, 2016

(86) PCT No.: PCT/US2016/025266
§ 371 (c)(1),
(2) Date: Sep. 27, 2017

(87) PCT Pub. No.: WO2016/161115
PCT Pub. Date: Oct. 6, 2016

(65) Prior Publication Data
US 2018/0075599 A1    Mar. 15, 2018

Related U.S. Application Data

(60) Provisional application No. 62/140,822, filed on Mar. 31, 2015, provisional application No. 62/159,695, filed on May 11, 2015.

(51) Int. Cl.
*G06K 9/00* (2006.01)
*G06T 7/00* (2017.01)
(Continued)

(52) U.S. Cl.
CPC .......... *G06T 7/0012* (2013.01); *G06T 1/0007* (2013.01); *G06T 7/40* (2013.01);
(Continued)

(58) Field of Classification Search
USPC ........ 382/100, 103, 106–107, 128–133, 162, 382/168, 173, 181, 199, 203, 209, 219,
(Continued)

(56) References Cited

U.S. PATENT DOCUMENTS 8,184,888 B2 * 5/2012 Lu ........................... G06T 7/143
382/131
8,369,593 B2 * 2/2013 Peng ..................... A61B 6/032
378/21
(Continued)

*Primary Examiner* — Seyed Azarian
(74) *Attorney, Agent, or Firm* — Quarles & Brady LLP

(57) ABSTRACT

A system and methods for detecting polyps using optical images acquired during a colonoscopy. In some aspects, a method includes receiving the set of optical images from the input and generating polyp candidates by analyzing the received set of optical images. The method also includes generating a plurality of image patches around locations associated with each polyp candidate, applying a set of convolutional neural networks to the corresponding image patches, and computing probabilities indicative of a maximum response for each convolutional neural network. The method further includes identifying polyps using the computed probabilities for each polyp candidate, and generating a report indicating identified polyps.

18 Claims, 8 Drawing Sheets

(51) Int. Cl.
 *G06T 1/00* (2006.01)
 *G06T 7/40* (2017.01)
 *A61B 6/02* (2006.01)

(52) U.S. Cl.
 CPC . *A61B 2576/02* (2013.01); *G06T 2207/10016* (2013.01); *G06T 2207/10068* (2013.01); *G06T 2207/30032* (2013.01)

(58) Field of Classification Search
 USPC ....... 382/232, 254, 274, 276, 287, 291, 305, 382/312; 378/4, 21, 41; 600/332, 343
 See application file for complete search history.

(56) References Cited

U.S. PATENT DOCUMENTS

| | | | | |
|---|---|---|---|---|
| 2009/0074270 A1* | 3/2009 | Tanaka | ............... | G06K 9/4609 382/128 |
| 2009/0074272 A1* | 3/2009 | Lu | ............... | G06T 7/0012 382/128 |
| 2010/0189326 A1* | 7/2010 | McGinnis | ............... | G06T 7/0012 382/131 |
| 2011/0135180 A1* | 6/2011 | Sugrue | ............... | G06T 5/50 382/131 |
| 2011/0206250 A1* | 8/2011 | McGinnis | ............... | G06T 7/0012 382/128 |

* cited by examiner

SYSTEM AND METHODS FOR AUTOMATIC POLYP DETECTION USING CONVULUTIONAL NEURAL NETWORKS

CROSS-REFERENCE TO RELATED APPLICATIONS

This application represents the national stage entry of PCT International Application No. PCT/US2016/025266 filed on Mar. 31, 2016 and claims priority to U.S. Provisional Application Ser. No. 62/140,822, filed Mar. 31, 2015, and U.S. Provisional Application Ser. No. 62/159,695 filed May 11, 2015, the contents of which are hereby incorporated by reference as if set forth in their entirety herein.

BACKGROUND

The present disclosure relates, generally, to systems and method for processing optical images. More particularly, the disclosure relates to automatic detection of polyps in optical images or video.

The colonoscopy is a preferred procedure for cancer screening and prevention, being widely accepted as effective for detecting colonic polyps, which are precursors to colon cancer. During the procedure, an endoscope fitted with a small camera is guided through a patient's colon to provide a real-time optical feed for diagnosis, biopsy and removal of polyps. As a result of colonoscopy use, the rate of incidence and mortality due to colon cancer has seen a significant decline.

However, the colonoscopy is an operator-dependent procedure, and as such relies on the effectiveness of the clinician to identify polyps. Hence, fatigue and insufficient attentiveness during examination, particularly during back-to-back procedures, often play a role in missing polyps. By some estimates the average polyp miss-rate is between 4 and 12%. Patients with missed polyps may be diagnosed with a late stage cancer with the survival rate of less than 10%. As such, the importance of reducing miss-rates cannot be over-emphasized.

Computer-aided polyp detection can provide a powerful tool to help reduce polyp miss-rate and encourage attentiveness during these procedures. To this end, algorithms have been developed to analyze in real-time the video feed acquired during the colonoscopy. Specifically, early attempts have focused on color and texture features to identify polyps in colonoscopy images. However, the effectiveness of such methods is limited due and color variations and texture visibility of polyps. More recent approaches have considered shape, or geometrical appearance features, such as elliptical-shaped features, or valley information to localize polyps. Yet other approaches have considered, spatio-temporal features.

As well known to those skilled in the art, computer-aided polyp detection based on the above approaches remains a challenging task. This is because various features appearing on a video feed can vary considerably, and depend on the camera viewing angle, depth of field, and illumination. For instance, polyp color can may have different colors, ranging from dark to saturated, depending on illumination. On the other hand, polyp texture becomes fully visible only if a given polyp appears within the depth of field of the camera. In addition, geometric features in the absence of contextual clues can be misleading. For example, valley information may result in false detections particularly around wrinkles and vascular structures. Furthermore, spatio-temporal features are only suitable for use in off-line processing, since information from the past and future frames are typically utilized.

In light of the above, there remains a need for systems and methods capable of accurately detecting polyps during a colonoscopy procedure.

SUMMARY

The present disclosure overcomes the aforementioned drawbacks by providing a system and methods for detecting polyps in optical colonoscopy images.

In one aspect of the disclosure, a system for polyp detection using optical images acquired during a colonoscopy is provided. The system includes an input configured to receive a set of optical images acquired from a patient during a colonoscopy, and a processor configured to process the series of optical images with steps comprising receiving the set of optical images from the input, and generating polyp candidates by analyzing the received set of optical images. The processor is also configured to process the images by generating a plurality of image patches around locations associated with each polyp candidate, applying a set of convolutional neural networks to the corresponding image patches, and computing probabilities indicative of a maximum response for each convolutional neural network. The processor is further configured to process the images by identifying polyps using the computed probabilities, and generating a report indicating identified polyps. The system further includes an output for displaying the report.

In another aspect of the disclosure, a method for detecting polyps using optical images acquired during a colonoscopy is provided. The method includes receiving the set of optical images from the input and generating polyp candidates by analyzing the received set of optical images. The method also includes generating a plurality of image patches around locations associated with each polyp candidate, applying a set of convolutional neural networks to the corresponding image patches, and computing probabilities indicative of a maximum response for each convolutional neural network. The method further includes identifying polyps using the computed probabilities for each polyp candidate, and generating a report indicating identified polyps.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Other aspects and advantages of the present disclosure will become apparent upon consideration, of the following detailed description and attached drawings.

DETAILED DESCRIPTION

Figure 1A:
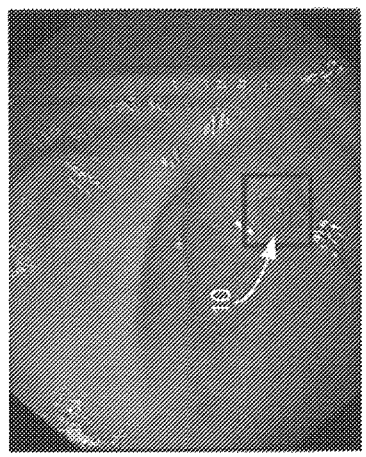
FIG. 1A are images showing limited texture visibility due to a relatively large distance between polyps and an imaging camera.
Figure 1A:
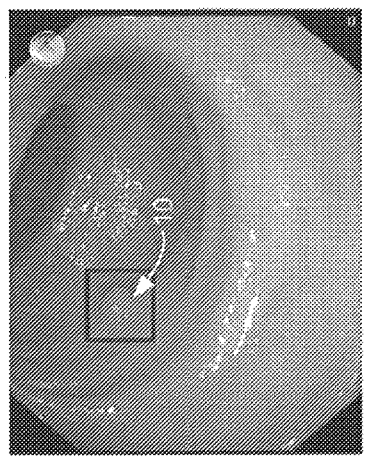
Figure 1A:
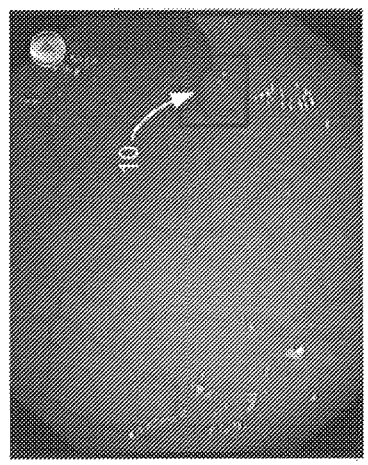
Figure 1B:
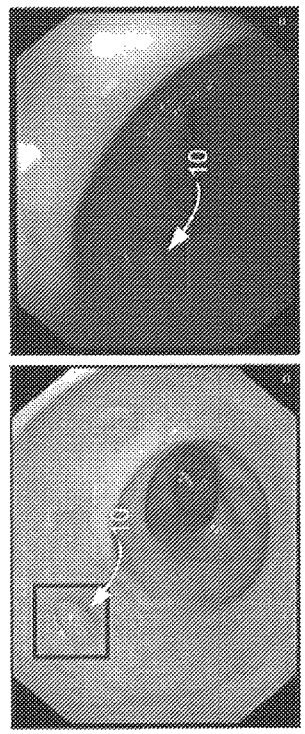
FIG. 1B are images showing significant color variation between two instances of the same polyp due to varying light conditions.
Figure 1C:
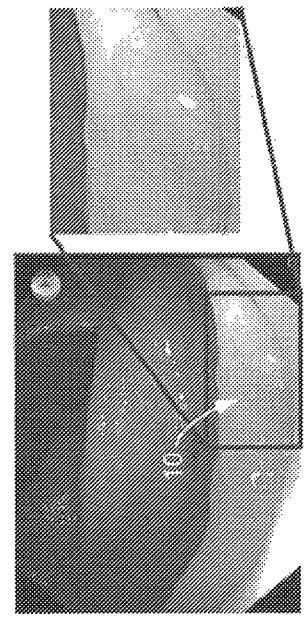
FIG. 1C are images showing a polyp with visible texture that appears within the depth of field of a camera.

The appearance or clues identifying polyps on a video feed acquired during a colonoscopy can vary either disappearing from view or coming into view, depending on the lighting conditions, angle and position of the camera relative to the polyps. For instance, as shown in FIG. 1A, a relatively large distance between a polyp 10 and camera leads to limited texture visibility. On the other hand, a polyp 10 appearing within the depth of view can provide visible texture, as shown in FIG. 1B. Similarly, FIG. 1C shows significant color variation between two instances of the same polyp 10 due to varying light conditions.

As appreciated from these examples, in some conditions, shape clues might be most reliable feature for polyp localization, such as when texture visibility is limited due to a polyp falling off the depth of field of the camera. On the other hand, at other instances of an examination, texture clues might be more reliable, such as when a texture-rich polyp clearly appears into view. In addition, other image clues might also provide information useful for the identification of polyp, as well as non-polyp structures. For instance, temporal information might be useful to distinguish polyps from other polyp-like structures, such as specular spots and air bubbles, which can appear briefly in a viewing scene.

The present disclosure recognizes the complementary nature of different image features, and the fact that during an examination, various image features may or may not be available or provide useful information. Therefore, rather than focusing only on specific polyp properties or image features, such as color, shape, or texture, as is common in the prior art, the present disclosure provides systems and methods that integrate various diverse properties to identify polyps. Specifically, the present approach makes use of convolutional neural networks ("CNNs") to learn and combine information from multiple image features, including color, shape, texture, and temporal features, into one consolidated framework. As will be described, this approach not only allows identification of colonic polyps with higher accuracy but also helps reduce polyp detection latency and number of false positives.

Turning now to FIG. 1, a block diagram of a polyp detection system 100, in accordance with aspects of the present disclosure, is illustrated. As shown, the polyp detection system 100 may generally include a colonoscopy device 102 or system and a controller 104 in communication with a colonoscopy device 104. In cooperation, the colonoscopy device 102 and controller 104 may be utilized to detect colonic polyps during a colonoscopy procedure.

In some embodiments, the colonoscopy device 102 may include an endoscope (not shown in FIG. 1) configured to acquire optical image data, either continuously or intermittently, from a patient's colon, and relay the optical image data to the controller 104 for processing and analysis. By way of example, the endoscope may include a CCD camera, fiber optic camera, or other video recording device, as well as one or more light sources. The endoscope may also include capabilities for treating or removing detected polyps, as well as capabilities for Obtaining biopsies from suspected lesions identified during the procedure. Other features may include air, water, and vacuum channels, and others known in the art. In some alternative implementations, the colonoscopy device 102 may also be in the form of a swallowable device, capable of imaging the gastro-intestinal tract, and more particularly the colon of a patient, as it passes through the body, as well as performing other functions.

As shown in FIG. 1, the polyp detection system 100 can optionally include a device positioning system 106 that is in communication with the colonoscopy device 102 via a wired or wireless connection. The device positioning system 106 is also in communication with the controller 104, and configured to send to and receive data and other signals therefrom, either wirelessly or via a wired connection. In some embodiments, the device positioning system 106 may be configured to monitor the position of the colonoscopy device 102, or a portion thereof. For instance, during examination of a patient's colon, the position of an endoscope tip or a swallowable device may be monitored by the device positioning system 106 and reported to the controller 104, in substantially real time. For example, the reported position may be relative to a coordinate system or relative to a location along a gastro-intestinal or colon tract, determined, for example, using anatomical images. The reported position may also be relative to a reference, such as a retracted position of an endoscope.

In some embodiments, the device positioning system 106 may also be configured to modify the position of the colonoscopy device 102. For example, the device positioning system 106 may be configured to advance as well as retract an endoscope, either at a predetermined rate, or as directed by the controller 104. As such, the device positioning system 106 may include a variety of mechanical components and hardware, to perform these, and other functions.

As shown in FIG. 1, the controller 104 can be a computer or workstation, as well as a network server, a mainframe or any other general-purpose or application-specific computing device. In some implementations, the controller 104 may also be a portable device, such as a mobile phone, laptop, tablet, personal digital assistant ("PDA"), multimedia device, or any other portable device. The controller 104 may also operate autonomously or semi-autonomously, or may receive instructions from a user, or any source logically connected to computer or device, such as another networked computer, device or server.

Figure 2:
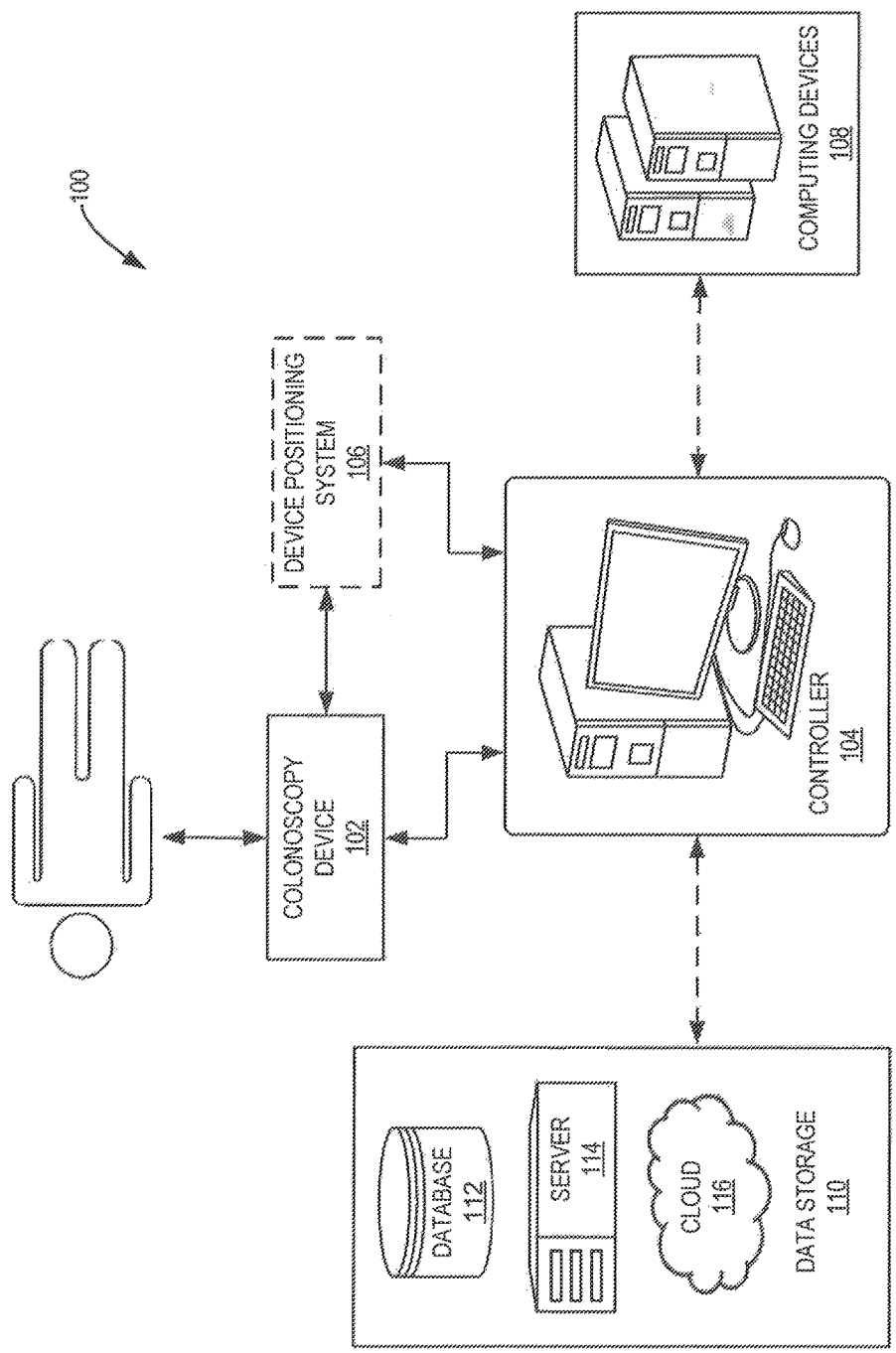
FIG. 2 is a schematic illustration of an example system for polyp detection, in accordance with aspects of the present disclosure.

As such, the controller 102 may also operate as part of, or in collaboration with one or more computers, systems, devices, machines, mainframes, servers and the like. For example, as shown in FIG. 1, the controller 104 may be in communication with various external computing devices 108, as well as various data storage 110 modules. Example data storage 110 modules may include one or more databases 112, data servers 114, and cloud 116, as shown in FIG. 2. In this regard, the controller 104 may be any computing device, apparatus or system, designed to integrate a variety of software and hardware capabilities and functionalities, as well as configured for carrying out steps in accordance with aspects of the disclosure.

In some implementations, the controller 104 may include at least one processor configured to acquire or access, and process optical image data, including optical image data obtained during a colonoscopy in order to detect colonic polyps. Example processors may include CPUs, GPUs and the like. In addition, the controller 104 may include various input elements configured for receiving optical image data, and other data, as well as various output elements for providing a report to a user or other system or device.

In particular, the input elements may be configured to receive a variety of information, data or selections from a user. As such, the input elements may be configured for selecting, entering or otherwise specifying parameters consistent with detecting polyps of a desired size, shape, color, texture, and other features. Example input elements may include a mouse, keyboard, touchpad, touch screen, buttons, and the like. Input elements of the controller 102 may also be configured to receive information or data directly from an imaging system or imaging device, such as the colonoscopy device 102, as well as from, one or more data servers, databases, cloud, internet and so forth, as indicated in FIG. 2. For instance, in some aspects, data received by the input elements includes optical image data, or video data obtained during a colonoscopy. Example input elements may include flash-drives, CD or DVD drives, USB or micro-USB inputs, HDMI inputs, an Ethernet or WIFI connection, and other inputs for receiving computer-readable media, data or signals.

In addition to being configured to carry out various steps for operating the polyp detection system 100 and components therein, the processor may also be configured to analyze optical image, and other data, to detect colonic polyps. In some aspects, such data analysis may be advantageously carried out in substantially real-time, while a colonoscopy is being performed. This would allow a clinician to take immediate action upon detection of a polyp. Alternatively, such data analysis may be carried out off-line by processing optical image data accessed from a data storage or memory. This would allow for automated verification of previously performed colonoscopies. To this end, the processor may read and execute software instructions from a non-transitory computer-readable medium, such as a hard drive, CD-ROM, DVD, internal, external or flash memory, and the like, as well as transitory computer-readable media.

In accordance with aspects of the present disclosure, the processor may be configured to process a set of optical colonoscopy images to identify polyp candidates. Specifically, the processor may be configured to apply an approach described by the inventors in US 2016/0078625, which is incorporated herein by reference in its entirety, to generate polyp candidates. In short, the processor may be configured to acquire or access optical image data using one or more inputs, and generate therefrom one or more edge maps consisting of a number of edge pixels. In some implementations, the edge maps may be generated based on filtered images. For example, filtered images may be obtained by applying red, green and blue color filters. One example method for generating edge maps includes Canny's method applied to different color filtered images. The processor may then refine the generated edge maps by using a classification scheme to remove as many non-polyp boundary pixels as possible from the generated edge maps. The retained edges may then be utilized by the processor in a voting scheme to generate voting maps whose maxima would indicate polyp candidate locations. In some aspects, bounding boxes corresponding to the identified polyp candidates may be determined according to the properties of the accumulated votes.

The processor may be further configured to utilize a framework based on deep CNNs to combine information from a complete set of image features, including color, shape, texture, and temporal features, and possibly other features. As such, in some aspects, the processor may be configured to train CNNs, using image data obtained from a population, or stored in a database. To identify polyps, the processor may generate multiple sets of image patches from a given colonoscopy image associated with an identified polyp candidate, as described above. Each set of patches corresponds to a different polyp feature, such as color, shape, texture, or temporal features. In addition, each set includes a number of patches generated at multiple scales and orientations. By way of example, three sets of patches may be generated based upon color and texture features, shape features, and temporal features. The generate patches may be resized, as well as normalized to a grayscale or histogram-equalized.

Then, each set of generated patches may be fed to the corresponding deep CNNs, with each patch being assigned a probabilistic score. The maximum probabilistic score for each set of patches may then be computed by the processor. A global probabilistic score fir the polyp candidate may then be computed by the processor by averaging the maximum probabilistic scores for each set of patches. In this manner, a confidence value for each polyp candidate can be generated, and provided, in a report by the processor, along with other information. The processor may be configured to carry out functions described above for a number of polyp candidates, either autonomously, or semi-autonomously using information or input provided by a user or obtained elsewhere.

In some implementations, the processor may receive positioning information from the device positioning system 106 and perform a number of functions. For example, the processor may process and/or report, via various output elements, positioning information provided by the device positioning system 106. The processor may further direct the device positioning system 106 to control the position of the colonoscopy device 102, depending upon identified polyps, as well as other information. The processor may also carry out processes associated with a medical intervention once polyps have been identified.

The output elements may take any shape or form, and may include various visual, audio and other systems for providing a report either intermittently or in substantially real time. For instance as shown, an output may be in the form of a display. Another output can include speakers. Yet another output can include one or more electronic connections through which signals, data, or reports can sent to a database, data storage, or a medical record, for example.

By way of example, the report may include visual information associated with a colonoscopy procedure. For instance, raw or processed optical images may be displayed, along with indicators and locations for identified objects, such as polyps, vessels, lumens, specular reflections, and so forth. The report may also indicate the probabilities or confidence scores for identified objects, such as colonic polyps. The report may also include an audio alert or signal to an operator upon identification of one or more polyps, or other objects. The report may further include instructions to the user for adapting the procedure, such as repeating or enhancing imaging of a particular anatomical location, or examining a previous anatomical location.

Figure 3:
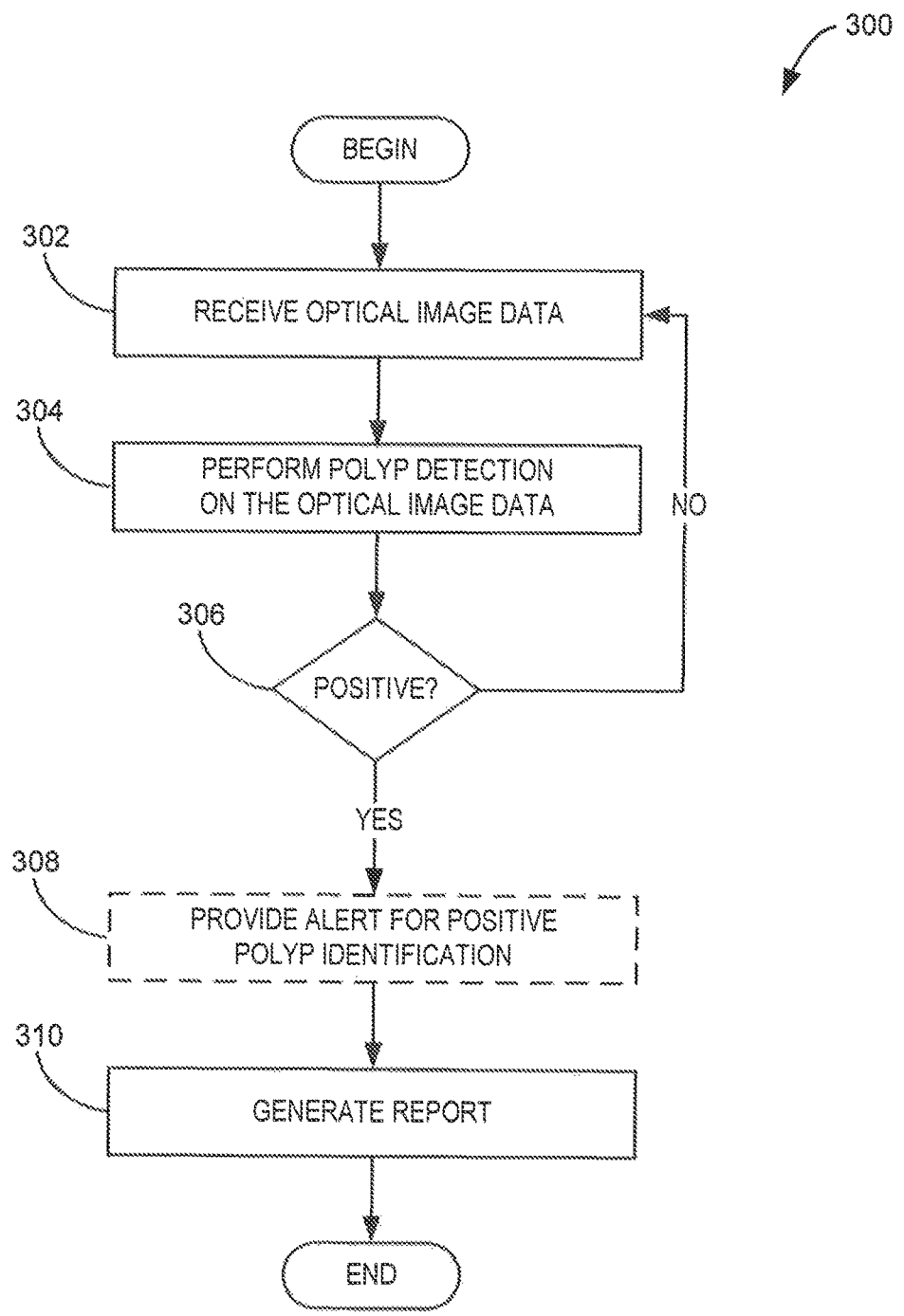
FIG. 3 is a flowchart setting forth steps of a process, in accordance with aspects of the present disclosure.

Turning to FIG. 3, steps of a process 300, in accordance with aspects of the present disclosure, are shown. In some implementations, the process 300 may be carried out using a polyp detection system 100 as described with respect to FIG. 2.

The process 300 may begin at process block 302 with optical image data or optical images being received. The optical image data may be provided from a live video feed acquired during a colonoscopy procedure. Alternatively, the optical image data may be accessed from a data storage location, memory, database, or cloud.

At process block 304, a polyp detection process may then be performed using the optical image data. In some aspects, a number of pre-processing steps may also be carried out at process block 304. For example, received optical image data may be assembled into a set of optical images. In addition, optical images may be filtered into various color channels. For example, red, green and blue color filters may be applied to the optical images. Other processing steps, may include normalizing image intensities, for instance using image histograms, resizing, as well as selecting various image portions or generating image patches or sub-patches. In the polyp detection process, a number of polyp candidates may be first identified by processing the optical image data, as described. The polyp candidates may then be utilized in a framework based on deep CNNs in order to identify colonic polyps. In particular, the CNNs are configured to combine information from multiple image features, including color, shape, texture, and temporal features, into one consolidated framework. This polyp detection process may be carried out for one or more images in a set of optical images acquired during a colonoscopy procedure.

Then, at process block 306, an evaluation is made whether polyps, or other targeted objects, have been identified. If not, process blocks 302 and 304 may be repeated, with additional optical images or data being received. If polyps, or other objects, are positively identified, then an alert may be provided to an operator to signify such positive identification, as indicated by process block 308. For example, the alert may be in the form of audio signals or visual displays, or instructions to the operator for adapting the colonoscopy procedure being performed. Subsequently, at process block 310, a report may then be generated. As described, the report may indicate polyp locations, along with confidence values or probabilities indicating the accuracy of detection. In some aspects, steps of the process 300 can be carried out continuously or intermittently, or for the duration of a colonoscopy procedure.

Figure 4:
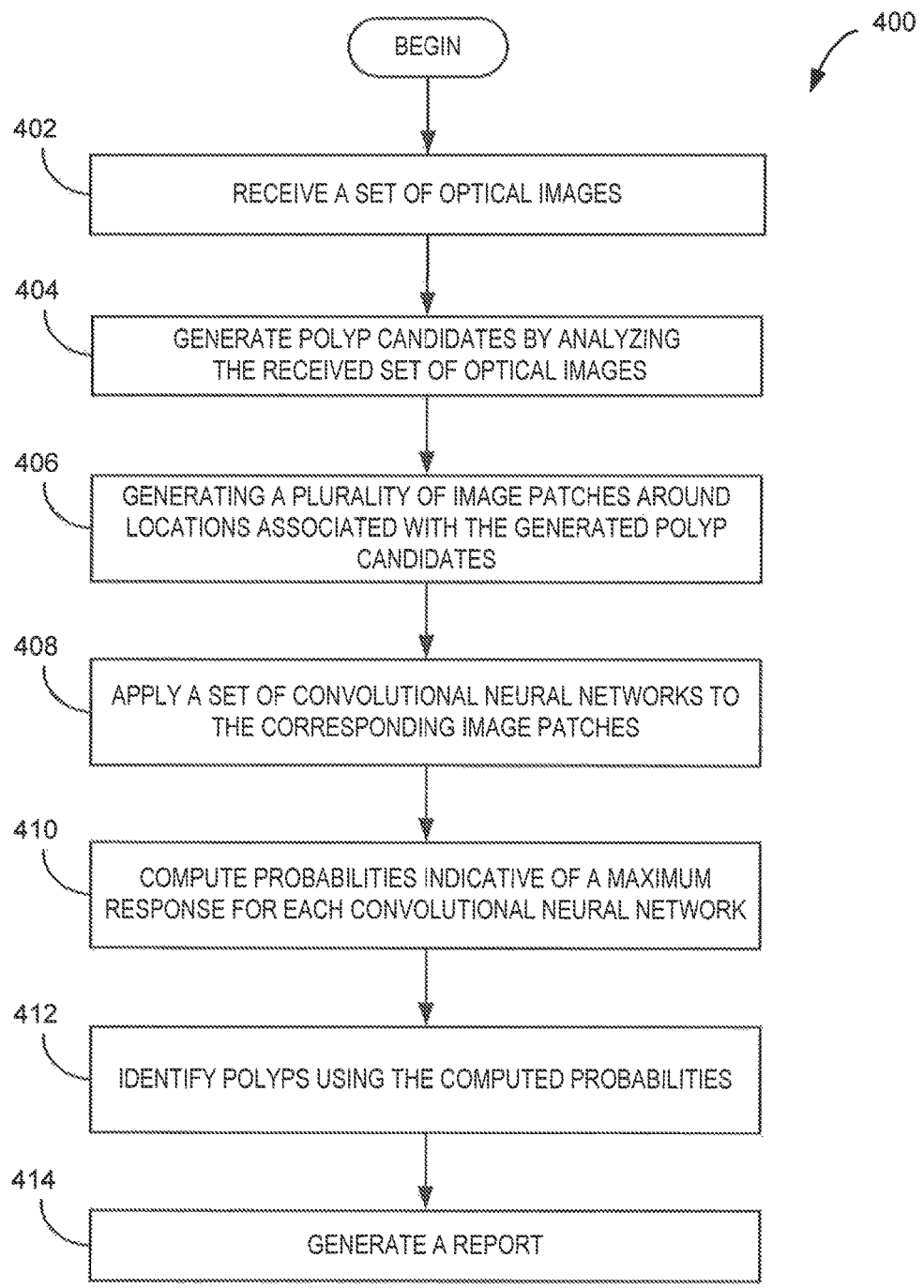
FIG. 4 is another flowchart setting forth steps of a process for polyp detection, in accordance with aspects present disclosure.

Turning now to FIG. 4 steps of a process 400 for performing polyp detection, in accordance with aspects of the present disclosure, are shown. In some implementations, process 400 may be carried out using a system described with reference to FIG. 2, or other suitable system.

The process 400 can begin at process block 402 with receiving one or more optical images for analysis. As described, such images can be obtained in substantially real-time from a live video feed or accessed from a data storage, memory, database, cloud, and the like. The optical images may then be analyzed to generate polyp candidates, as indicated by process block 404. In the analysis, the images may be processed to construct one or more edge maps, for example, by applying Canny's method of edge detection, for example. Advantageously, different color channels associated with the received images may be analyzed to extract as many edge pixels as possible. As such, the received images may be filtered using various color filters, such as red, blue, an green color filters. Edge pixels obtained using the different color channels may then be combined to generate the edge maps. The edge maps may be further refined by applying a classification scheme based on patterns of intensity variation, and used in a voting scheme, as described, to identify polyp candidates. In some aspects, a bounding box is generated for each identified polyp candidate.

Then, at process block 406, a plurality of images patches may be generated around locations corresponding to the identified polyp candidates. In some aspects, the locations are determined based on the bounding boxes obtained at step 404. For a given polyp candidate, multiple sets of image patches may be generated, each set corresponding to a different polyp feature, such as color, shape, texture, and temporal features. In addition, each set may include various patches generated at multiple scales and orientations. In some aspects, color patches may be normalized to a grayscale and/or histogram-equalized, as well as resized.

Then, at process block 408, a set of CNNs are applied to the corresponding image patches, and probabilities indicative of a maximum response for each CNN are computed, as indicated by process block 410. That is, each patch is assigned a probabilistic score. The maximum probabilistic score for each set of patches may then be computed, and a global probabilistic score may then be computed by averaging the maximum probabilistic scores for each set of patches. In this manner, a confidence value for each polyp candidate can be generated. Based on such candidate, polyps can be identified, as indicated by process block 412.

A report is then generated, at process block 414. As described, the report may provide audio and/or visual information. For instance, raw or processed optical images may be displayed, along with indicators and locations for identified objects, such as polyps, vessels, lumens, specular reflections, and so forth. The report may also indicate the probabilities or confidence scores for identified objects, including colonic polyps. The report may also include an audio alert or signal to an operator upon identification of one or more polyps, or other objects. The report may further include instructions to the user for adapting the procedure, such as repeating or enhancing imaging of a particular anatomical location, or examining a previous anatomical location described.

Figure 5:
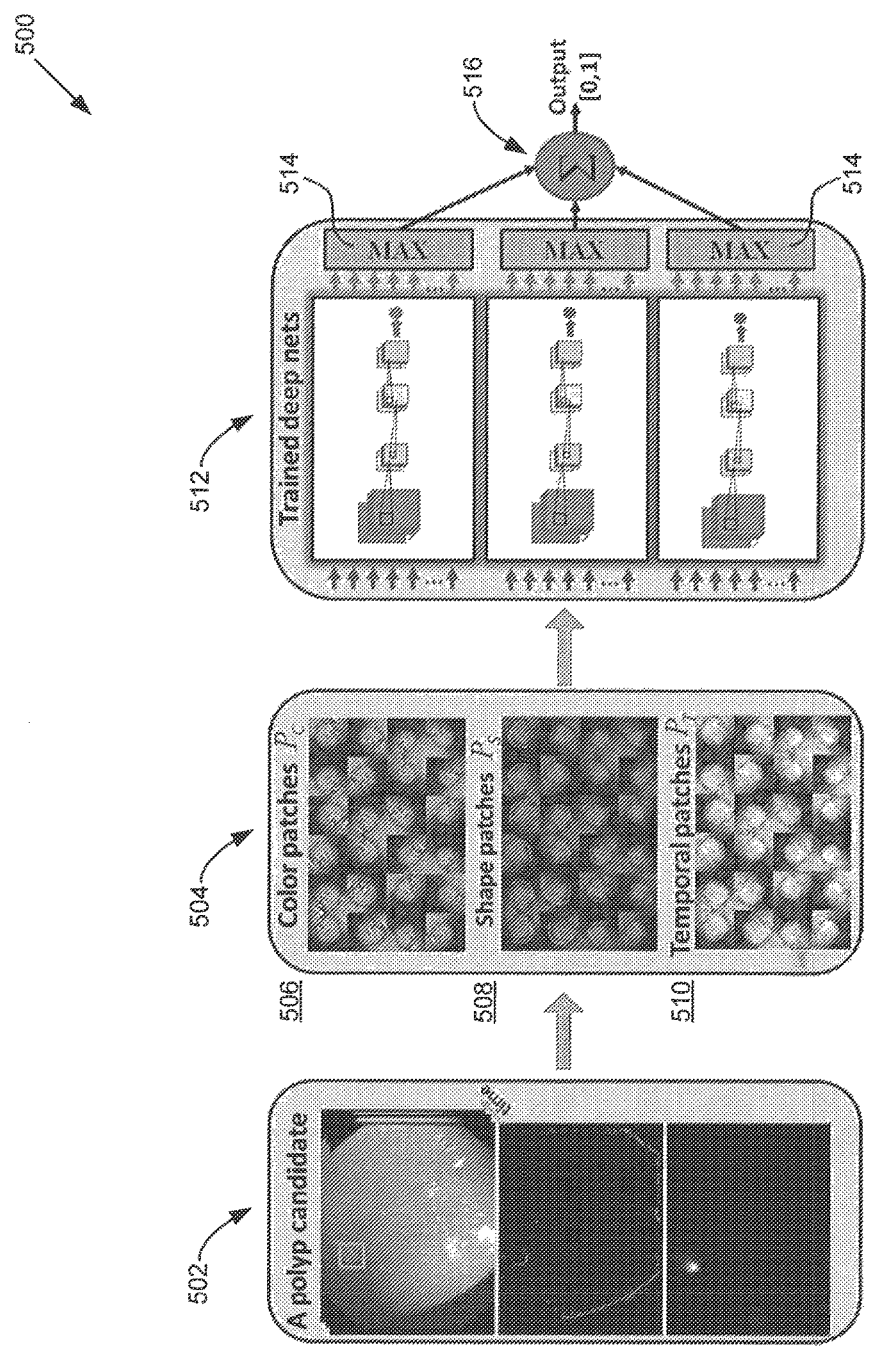
FIG. 5 is an illustration showing a process for probabilistic score generation and fusion based on convolutional neural networks, in accordance with the present disclosure.

The above polyp detection process is illustrated in FIG. 5. That is, at step 502, a polyp candidate is generated by processing an optical image as described. Using the location of the polyp candidate, a number of image patches are generated at step 504, including a set of color patches 506, a set of shape patches 508 and a set of temporal patches 510. Then, at step 512, trained deep nets, or CNNs, are then applied to the image patches, generating probabilistic scores 514, as shown. Then computed probabilities scores 514 may then be combined, or averaged, to generate a global confidence score 516, indicative of whether the identified polyp candidate is a polyp.

The key to optimal feature extraction and aggregation is to determine what image presentations best reveal the desired features for the subsequent convolutional networks. For color and texture, histogram-equalized color patches were collected from a given frame. Experiments showed that partial illumination invariance, achieved by histogram equalization, significantly improved the accuracy of the subsequent CNN. For shape in context, 3-channel patches were constructed by stacking the gray channel of the current frame and the corresponding refined edge channel and voting channel generated using a previous technique by the inventors. In some aspects, the refined edge map may be preferred over the original edge map because the latter may contain a large amount of spurious edges associated with specular spots (particularly on polyp surfaces) that can disrupt learning the essential shape information of polyps. For temporal features, 3-channel patches were constructed by stacking histogram-equalized gray channel of the current frame and that of the previous 2 frames. Unlike previous approaches, information from the future frames was not included. This is because in a real-time detection system, future frames may not be available.

In the present disclosure it is recognized that deep neural networks may be advantageously utilized to learn a multi-scale set of image features and a discriminative classifier during a supervised training process, eliminating the need for designing hand crafted-features and tuning the corresponding parameters. In some aspects, Krizhevsky's GPU implementation of CNNs may be utilized to deeply mine the above explained sets of patches in search for an optimal set of features and classifiers.

In addition to descriptions above, specific examples are provided below, in accordance with the present disclosure. These examples are offered for illustrative purposes only, and are not intended to limit the scope of the present invention in any way. Indeed, various modifications in addition to those shown and described herein will become apparent to those skilled in the art from the foregoing description and the following example and fall within the scope of the appended claims.

EXAMPLE

A set of 40 short colonoscopy videos were collected, of which half were positive and half were negative shots. A positive shot was defined as a sequence of frames that showed a unique polyp from different view angles. A negative shot was defined as a segment of colonoscopy video that did not contain a polyp. An annotated polyp database, consisting of approximately 7,000 frames with polyps and 28,000 frames without polyps, was utilized. For each frame that contained a polyp, a ground truth image was created where the polyp region was shown in white and background in black. For evaluation, a detection was considered as a true (false) positive if it fell inside (outside) the white region of the ground truth image. For consistency with previous work, a test set consisted of the positive shots and a random subset of negative shots, which was needed for a solid false positive analysis.

To train the CNNs, a polyp detection method using a CVCColonDB database was applied, similar to previous work done by the inventors. All the generated polyp candidates were grouped into true and false detections according to the available ground truth for the training videos. Next, three sets of patches, were collected around polyp candidates, namely color patches (PC), shape patches (PS) and temporal patches (PT). Patches that were extracted around true detections were labeled positive and the rest were labeled as negative. To learn the polyp features in context, each of the above sets as collected in multiple scales. Furthermore, since CNNs require a large amount of training data, data augmentation was performed by extracting patches at multiple orientations and translation in each given scale. Specifically, given a candidate location and the corresponding detection bounding box, patches were extracted in 3 scales with the size of patches being 1.1, 1.2, and 1.4 times the size of the detection bounding box. For translation, the patch window was translated by 10% in north, west, south, and east directions, resulting in 4 addition patches at each scale. For rotation, 90-degree rotations were applied on the collected patches followed by horizontal and vertical flipping, resulting in a total of 8 patches for each combination of scale and translation. In summary, each of the above sets contained 120 patches (3×8×5) for each polyp candidate, totaling 400000 patches for the entire training dataset. Lastly, all collected patches, regardless of their original scale, were reamed to 32×32 pixels.

Figure 6:
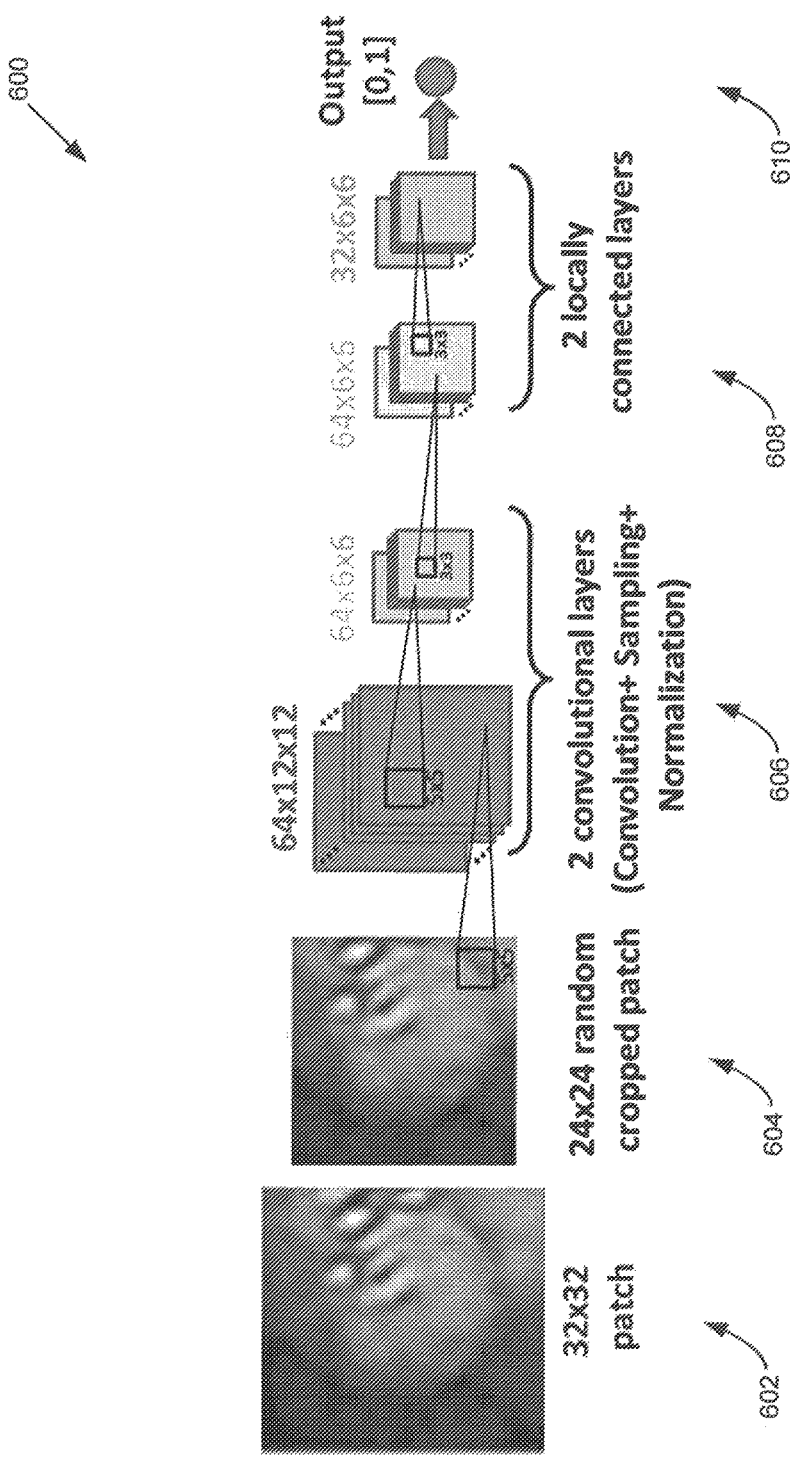
FIG. 6 is an illustration showing a network layout for a deep convolutional neural network, in accordance with the present disclosure.

FIG. 6 illustrates the network layout applied for CNNs utilized this study. A common practice when training CNNs includes randomly cropping smaller patches from the original training patches. Such an image cropping mechanism achieves partial robustness against small image translation and also helps avoid over-fitting to the training data. Following this practice, the network shown in FIG. 6 begins with taking a 24×24 sub-patch 604 from random locations in the 32×32 original patch 602. The network then follows by 2 convolution blocks 606 and 2 locally connected layers 608. Each of the convolution blocks 606 is comprised of a convolution layer with rectified linear activation functions followed by a local normalization layer and a max pooling layer with a down-sampling factor of 2. The first convolution layer learns 5×5 discriminative patterns from each channel of the training patches. The second convolution layer learns 5×5 filters as well, but from the feature maps generated in the first convolution block. The last 2 locally connected layers 608 have no weight sharing and thus each learns 1152 filters of size 3×3.

Figure 7A:
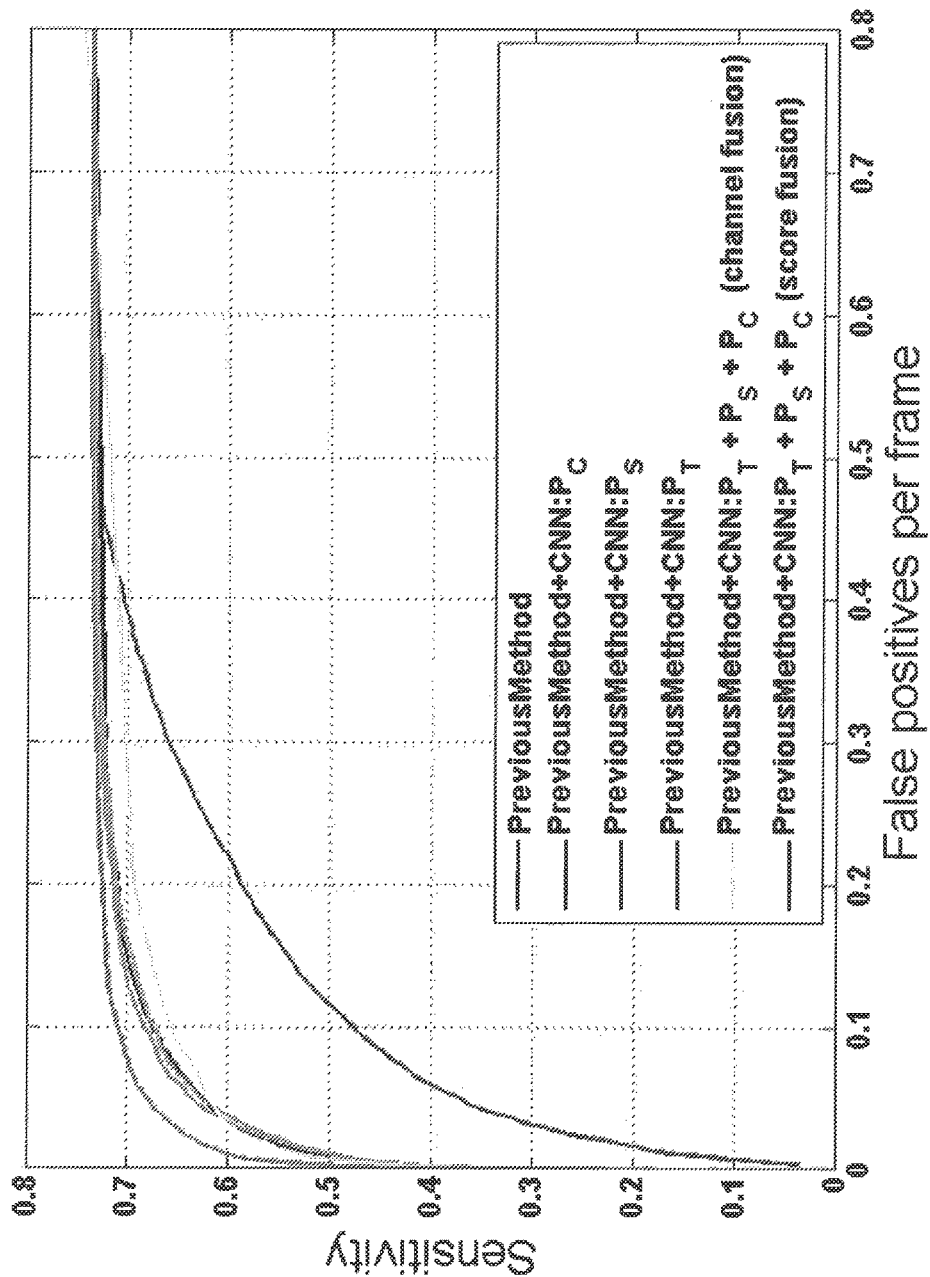
FIG. 7A is a graph comparing sensitivity versus false positive detection for the present approach relative to previous techniques.
Figure 7B:
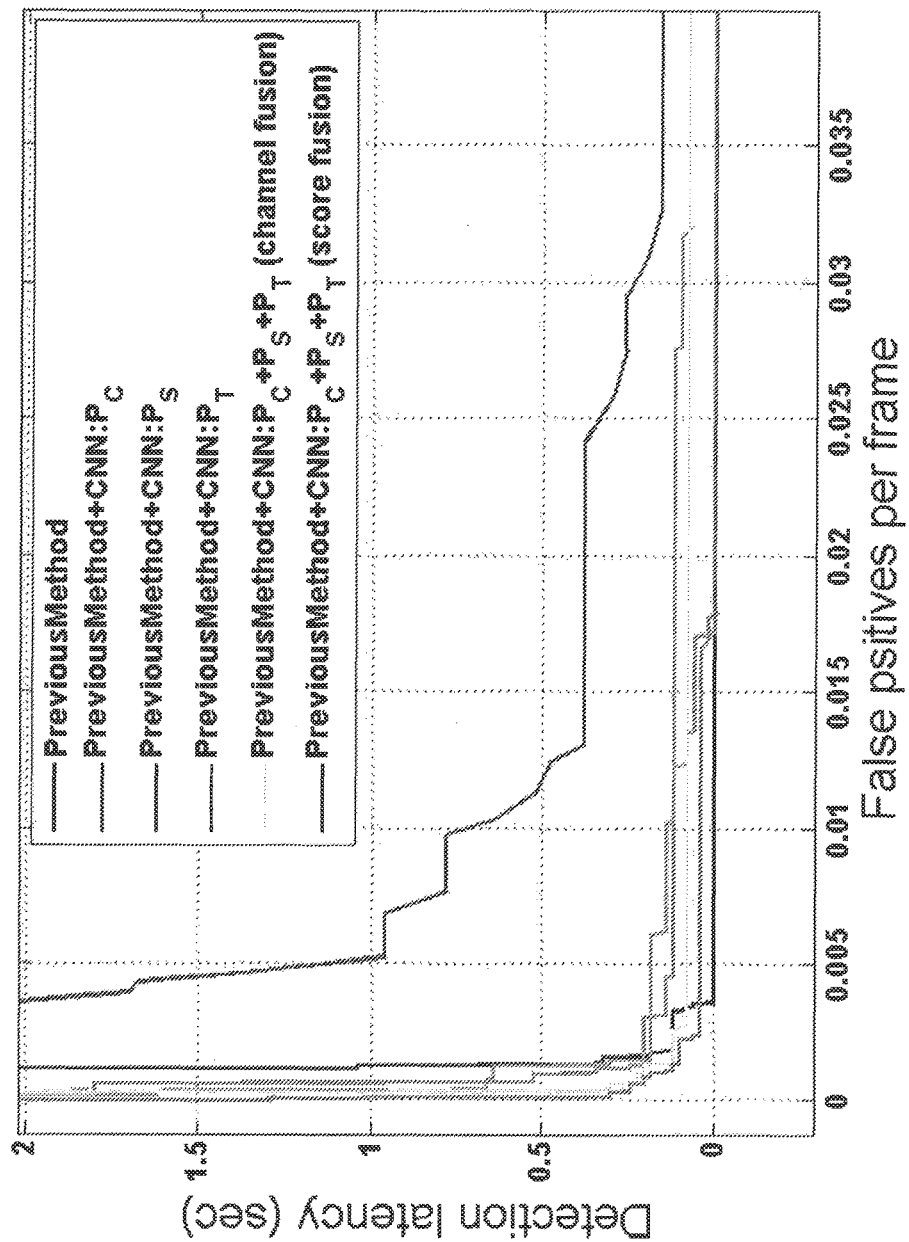
FIG. 7B is another graph comparing detection latency versus false positive detection for the present approach relative to previous techniques.

Advantages of the present approach may be appreciated form FIGS. 7A and 7B. Specifically, FIG. 7A compares free response operating characteristics ("FROCs") of a previous method developed by the inventors for determining polyp candidates, with the approach of the present disclosure. FROC analysis is widely used for evaluating computer-aided detection systems. Therefore, FROCS were obtained for CNNs trained on color patches (PC), temporal patches (PT), and shape in context patches (PS), as well as combinations. Specifically, two different fashions namely "score fusion" and "channel fusion" were utilized. Score fusion is illustrated in FIG. 5, whereby three distinct CNNs each specialized in one type of feature was utilized. Alternatively, channel fusion was performed by stacking color, shape, and temporal patches for each polyp candidate followed by training one CNN.

As seen from FIG. 7A, while each of the trained CNNs significantly improved performance compared to the previous method (p<0:0001, JAFROC test), the best result was obtained using score fusion framework, with the number of false positives being reduced by a factor of 50 at 50% sensitivity and by a factor of 22 at 60% sensitivity. The score fusion approach generated 0.002 false positives per frame at 50% sensitivity, a significant performance improvement compared to a previous technique, which produced 0.15 false positives per frame at the same sensitivity. On the other hand, the channel fusion framework yielded only comparable performance in low sensitivity and was outperformed at higher sensitivity. This may be attributed to the effects of dimensionality, since stacking all available image channels increases the dimension of feature space.

The above-presented FROC analysis does not consider the factor of time, and is simply measures polyp sensitivity in the provided video data. While it is desirable for a computer-aided polyp detection system to localize as many instances of a polyp as possible with high accuracy, it is also important to measure how quickly polyps are detected. This is because the longer the polyps stay in the view, the more likely a clinician can detect them on their own. Therefore, a performance curve more amenable to the colonoscopy procedure was utilized. Specifically, the detection latency was computed with respect to the number of false positives per frame according to $$\Delta T = (t_2 - t_1)/f_{ps} \qquad (1)$$

where $t_1$ is the arrival frame of the polyp, $t_2$ is the frame in which the polyp was detected, and $f_{ps}$ is the frame rate of the video. As with FROC, a threshold on the detection results was changed, and then at each operating point measured the median polyp detection latency of the test positive shots and the number of false positives in the entire test set. As seen in FIG. 7B, while augmenting the previous method with each individual CNN significantly improved promptness, the best performance was observed for color features and the score fusion approach described.

In summary, a novel system and method for polyp detection was described herein. The present approach is distinct from the previous works in that it does not rely on one or only a subset of polyp properties. Rather, it fully utilizes all the available image features including color, texture, shape, and temporal features. Evaluations based on a large annotated polyp database demonstrated a superior performance over the state-of-the-art methods available, significantly reducing polyp detection latency and false positives without sacrificing sensitivity. Such a remarkable performance improvement is attributable to the unique 3-way image presentation and effective use of aggregated convolutional neural networks.

The present invention has been described in terms of one or more preferred embodiments, and it should be appreciated that many equivalents, alternatives, variations, and modifications, aside from those expressly stated, are possible and within the scope of the invention.

The invention claimed is:

1. A system for polyp detection using optical images acquired during a colonoscopy, the system comprising:
   an input configured to receive a set of optical images acquired from a patient during a colonoscopy;
   a processor configured to process the series of optical images with steps comprising:
   i. receiving the set of optical images from the input;
   ii. generating polyp candidates by analyzing the received set of optical images;
   iii. generating a plurality of image patches around locations associated with the generated polyp candidates;
   iv. applying a set of convolutional neural networks to the corresponding image patches;
   v. computing probabilities indicative of a maximum response for each convolutional neural network;
   vi. identifying polyps using the computed probabilities, wherein the processor is further configured to compute a confidence score for each polyp candidate using the computed probabilities;
   vii. generating a report indicating identified polyps; and
   an output for displaying the report.

2. The system of claim 1, wherein the processor is further configured to construct edge maps corresponding to the set of optical images, each edge map comprising a plurality of edge pixels.

3. The system of claim 2, wherein the processor is further configured to generate refined edge maps by applying a classification scheme based on patterns of intensity variation to the plurality of edge pixels in each edge map.

4. The system of claim 3, wherein the processor is further configured to perform a voting scheme using the refined edge maps to identify the polyp candidates.

5. The system of claim 1, wherein the plurality of image patches comprises color patches, shape patches and temporal patches.

6. The system of claim 1, wherein the plurality of image patches are generated at multiple scales and orientations.

7. The system of claim 1, wherein the confidence score is computed using an average of the computed probabilities for each polyp candidate.

8. The system of claim 7, wherein the polyps are identified by the processor based on respective confidence scores.

9. The system of claim 1, wherein the processor is further configured to determining a bounding box indicating the extents of each polyp candidate.

10. A method for detecting polyps using optical images acquired during a colonoscopy, the method comprising:
    a) receiving the set of optical images from the input;
    b) generating polyp candidates by analyzing the received set of optical images;
    c) generating a plurality of image patches around locations associated with the generated polyp candidates;
    d) applying a set of convolutional neural networks to the corresponding image patches;
    e) computing probabilities indicative of a maximum response for each convolutional neural network;
    f) identifying polyps using the computed probabilities for each polyp candidate, wherein the method further comprises computing a confidence score for each polyp candidate using the computed probabilities;
    g) generating a report indicating identified polyps.

11. The method of claim 10, the method further comprising constructing edge maps corresponding to the set of optical images, each edge map comprising a plurality of edge pixels.

12. The method of claim 11, the method further comprising generating refined edge maps by applying a classification scheme based on patterns of intensity variation to the plurality of edge pixels in each edge map.

13. The method of claim 12, the method further comprising performing a voting scheme using the refined edge maps to identify the polyp candidates.

14. The method of claim 10, wherein the plurality of image patches comprises color patches, shape patches and temporal patches.

15. The method of claim 10, wherein the plurality of image patches are generated at multiple scales and orientations.

16. The method of claim 10, wherein the confidence score is computed using an average of the computed probabilities for each polyp candidate.

17. The method of claim 16, wherein the polyps are identified based on respective confidence scores.

18. The method of claim 10, wherein the method further comprises determining a bounding box indicating the extents of each polyp candidate.

* * * * *

UNITED STATES PATENT AND TRADEMARK OFFICE
CERTIFICATE OF CORRECTION

PATENT NO. : 10,055,843 B2
APPLICATION NO. : 15/562088
DATED : August 21, 2018
INVENTOR(S) : Nima Tajbakhsh et al.

It is certified that error appears in the above-identified patent and that said Letters Patent is hereby corrected as shown below:

On the Title Page

Item (54), Title, Line 3, "CONVULUTIONAL" should be --CONVOLUTIONAL--.

In the Specification

Column 1, Line 3, "CONVULUTIONAL" should be --CONVOLUTIONAL--.

Column 6, Line 34, "fir" should be --for--.

Column 10, Line 4, "hounding" should be --bounding--.

Column 10, Line 16, "reamed" should be --resized--.

Signed and Sealed this
Sixth Day of November, 2018

Andrei Iancu
*Director of the United States Patent and Trademark Office*